United States Patent [19]
Lubin

[11] Patent Number: 5,324,326
[45] Date of Patent: Jun. 28, 1994

[54] PRESSURE SENSING PACING LEAD

[75] Inventor: Mark Lubin, Miami, Fla.

[73] Assignee: Telectronics Pacing Systems, Inc., Englewood, Colo.

[21] Appl. No.: 796,767

[22] Filed: Nov. 25, 1991

[51] Int. Cl.$^5$ .................................. A61N 1/05
[52] U.S. Cl. .................................. 607/122; 128/675
[58] Field of Search .................. 128/673, 675, 786

[56] References Cited

U.S. PATENT DOCUMENTS

| | | | |
|---|---|---|---|
| 4,566,456 | 1/1986 | Koning et al. | 128/419 PG |
| 4,708,143 | 11/1987 | Schroeppel | 128/419 PG |
| 4,967,755 | 11/1990 | Pohndorf | 128/675 |
| 5,005,587 | 4/1991 | Scott | 128/786 |
| 5,137,019 | 8/1992 | Pederson et al. | 128/734 |

OTHER PUBLICATIONS

A. D. Sharma et al., "Right Ventricular Pressure During Ventricular Arrhythmias in Humans: Potential Implications for Implantable Antitachycardia Devices," *JACC*, vol. 15, No. 3, pp. 648–655 (Mar. 1, 1990).

*Primary Examiner*—William E. Kamm
*Assistant Examiner*—Scott M. Getzow
*Attorney, Agent, or Firm*—Gottlieb, Rackman & Reisman

[57] ABSTRACT

An elongate endocardial lead is disclosed which includes at least one distal electrode for sensing electrical activity in, and delivering electrical pacing pulses to, a patient's malfunctioning heart, a plurality of proximal terminal pins for coupling the lead to a pacemaker device, and a distal pressure sensor for sensing haemodynamic pressure within the heart. The pressure sensor comprises an integrated circuit chip having a layer of piezo-resistive material and a non-conductive base member, with the layer of piezo-resistive material being carried by the base member and having a pressure sensing diaphragm area therein exposed to ambient pressure. The base member and layer of piezo-resistive material are constructed and arranged so as to form a hermetically sealed chamber therebetween, with the chamber being at substantially atmospheric pressure and being substantially coextensive with the pressure sensing diaphragm area. The lead further includes coil wire conductors for coupling the integrated circuit chip and electrodes to various ones of the proximal terminal pins, so that a central lumen is provided in the lead throughout a major portion of the length thereof to facilitate passage of a stylet therethrough for actuating a device at the distal end of the lead to fix the lead to tissue of the heart.

11 Claims, 11 Drawing Sheets

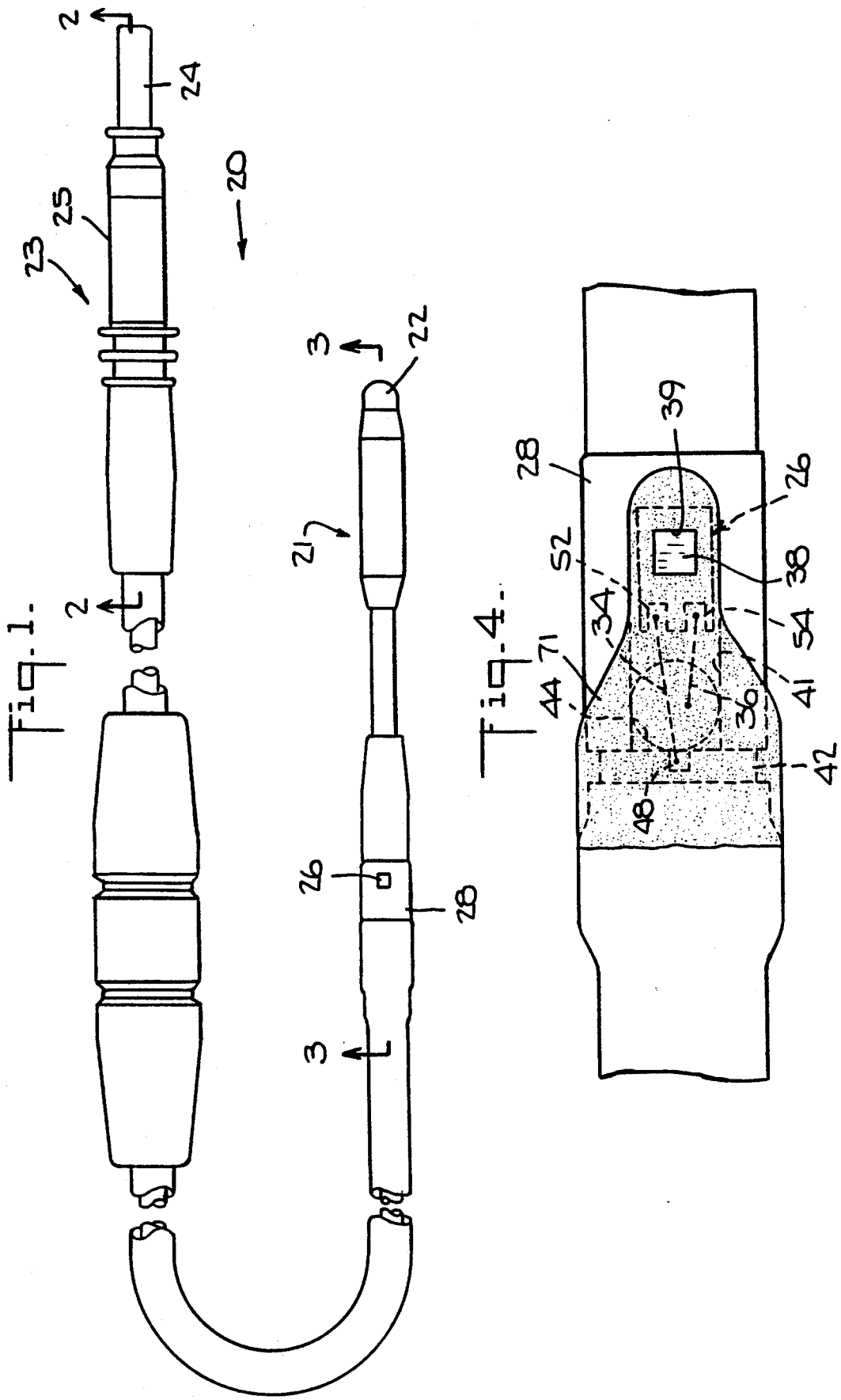

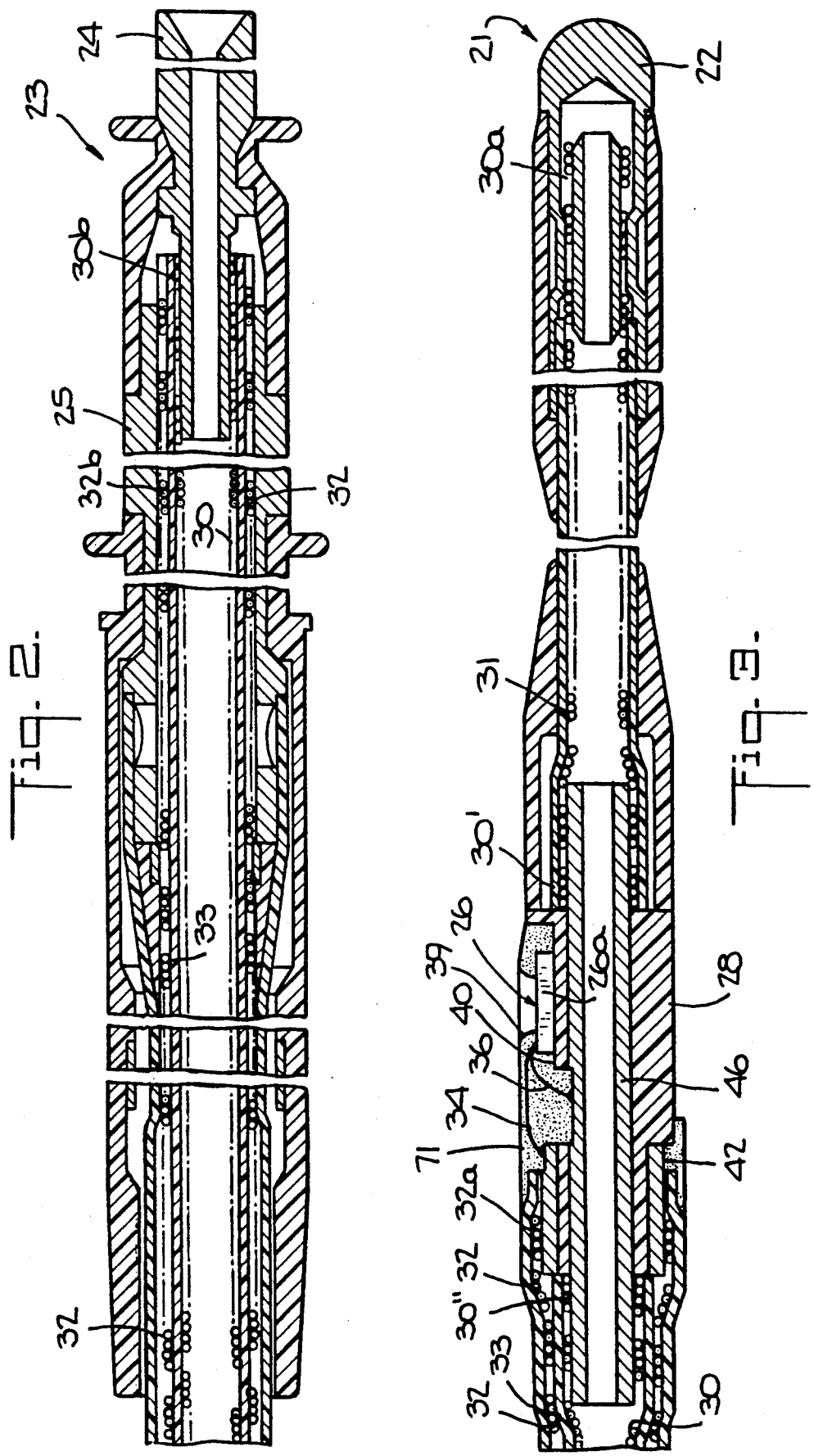

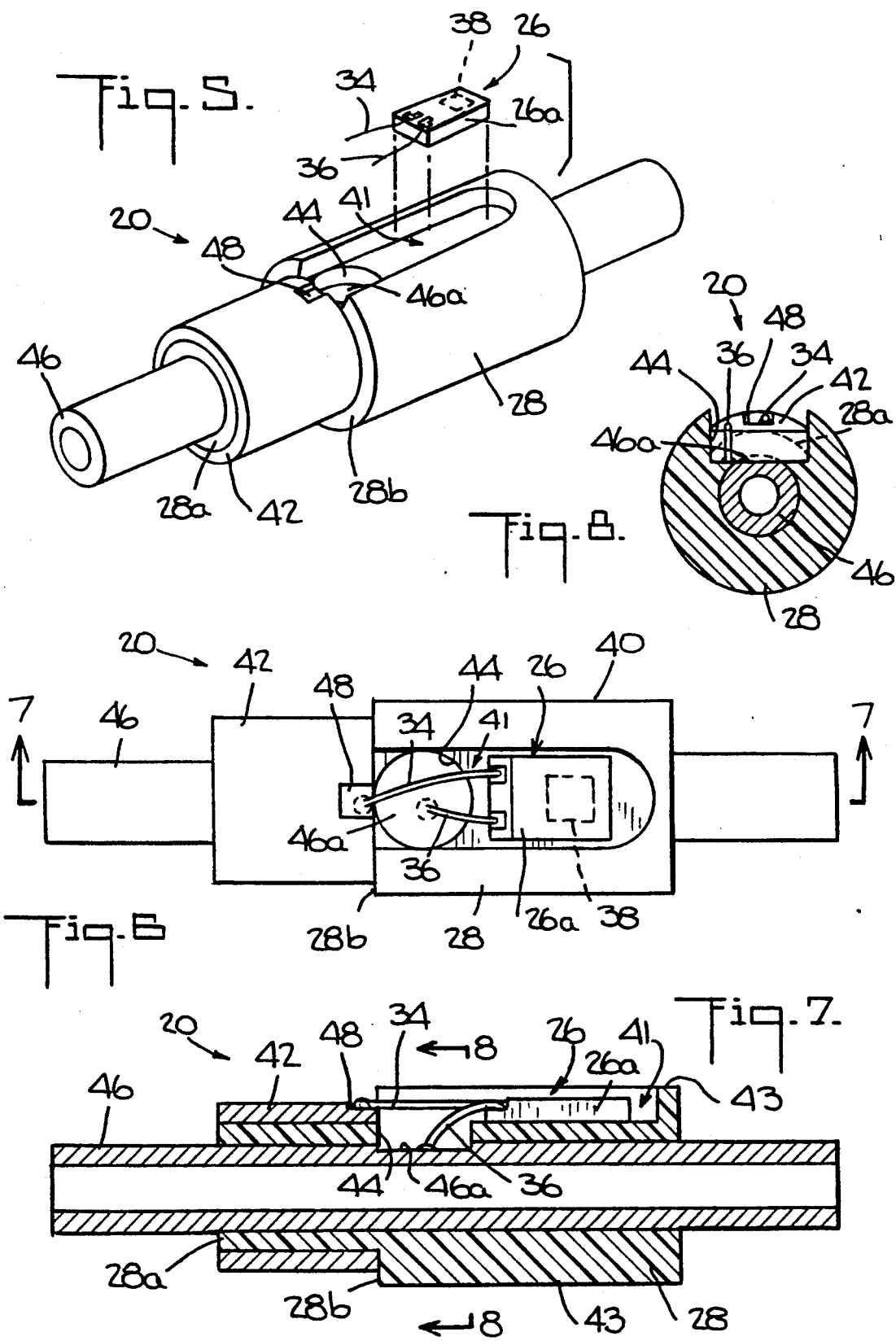

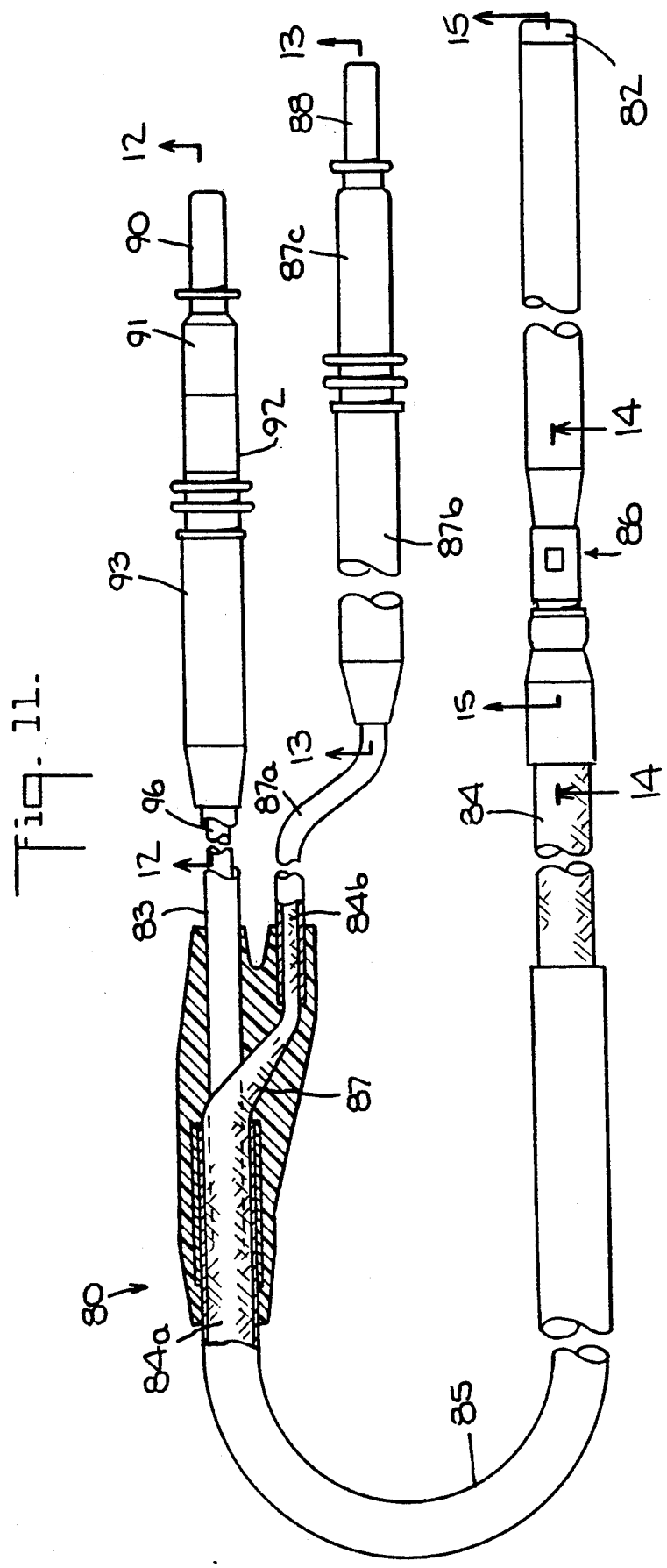

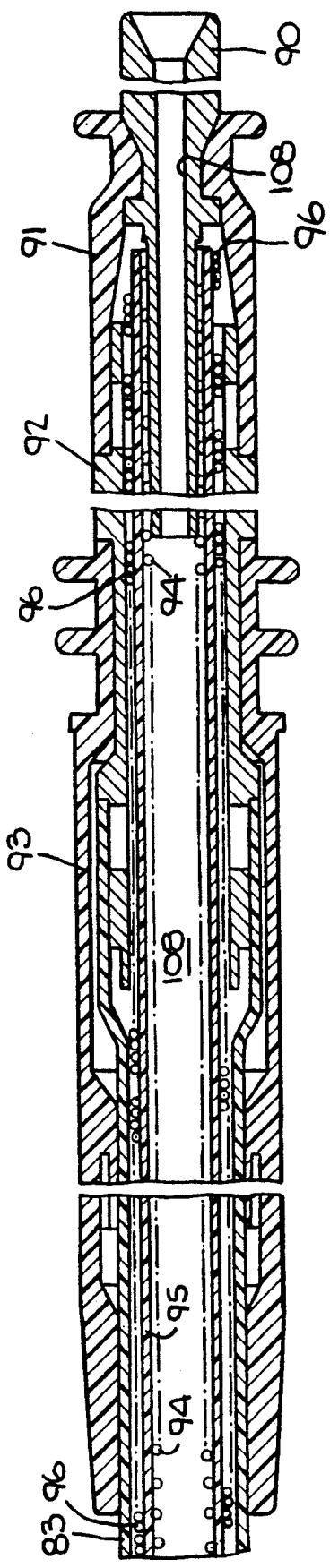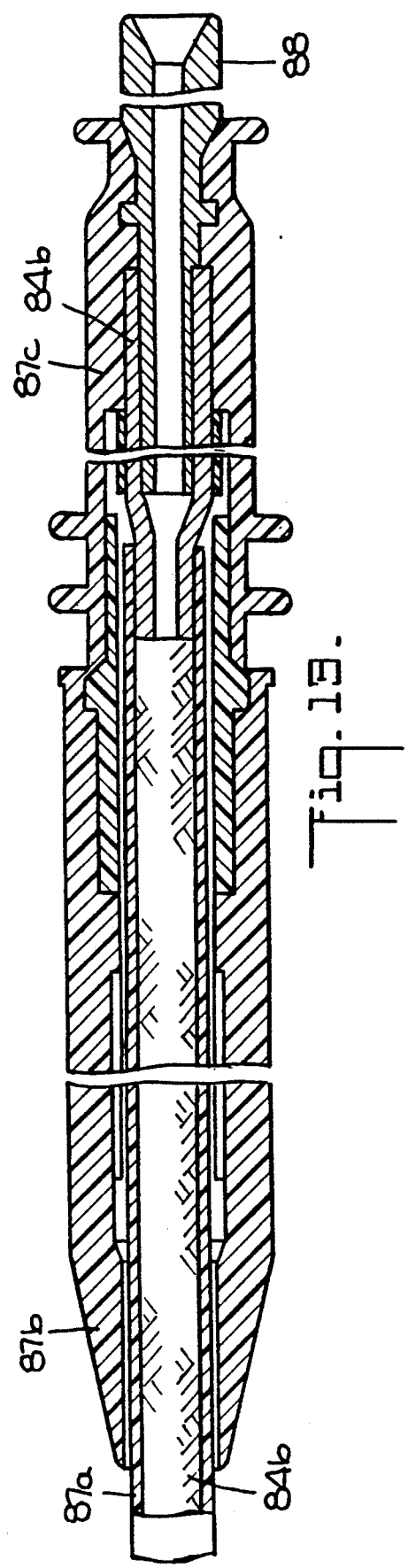
Fig. 12.
Fig. 13.

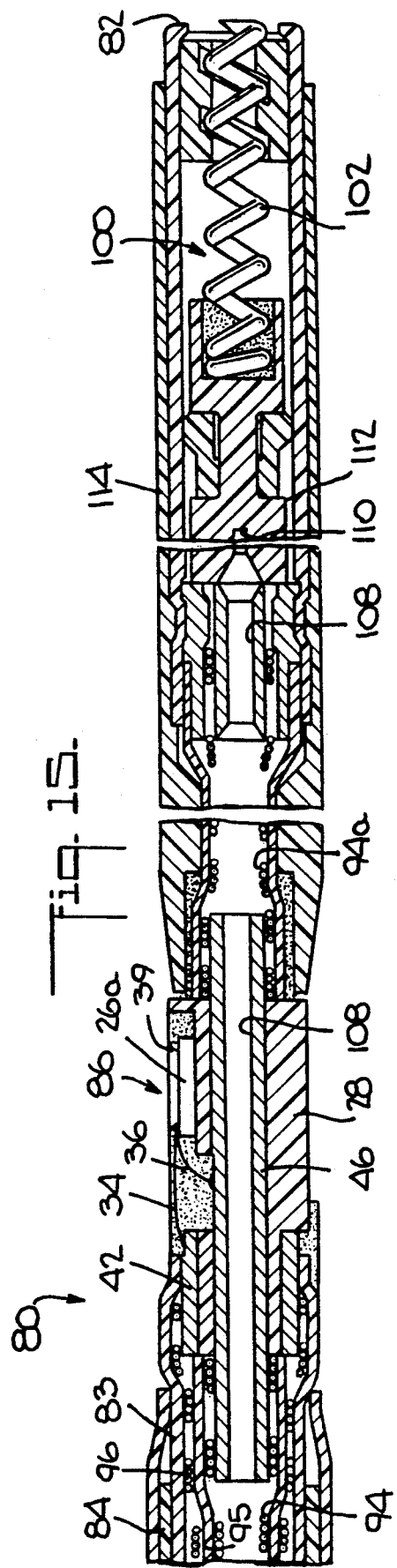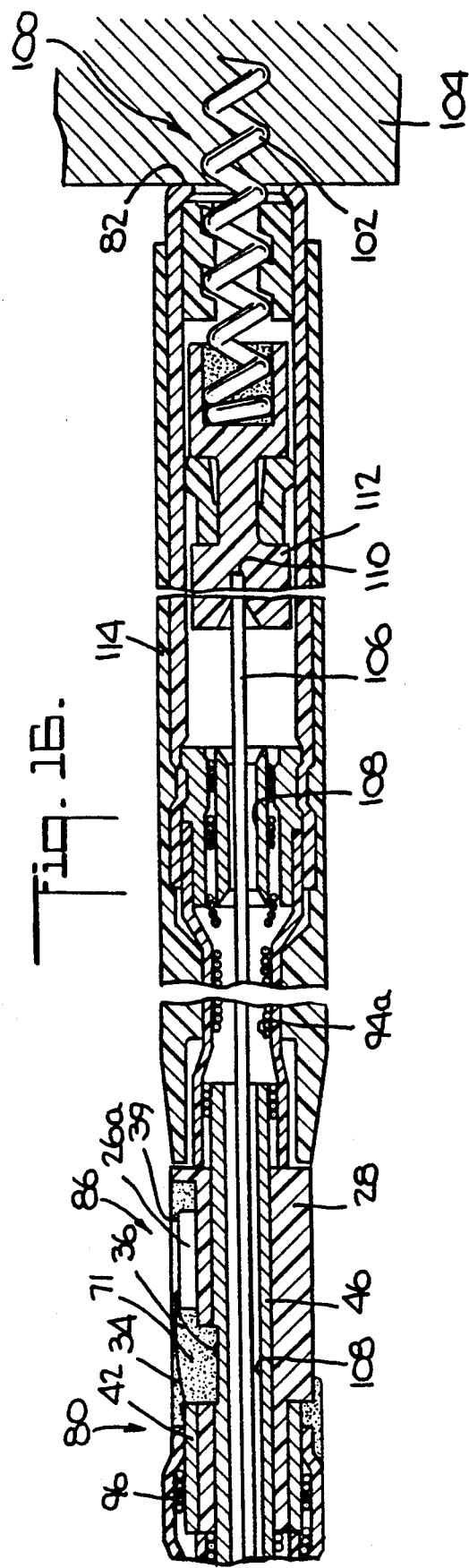

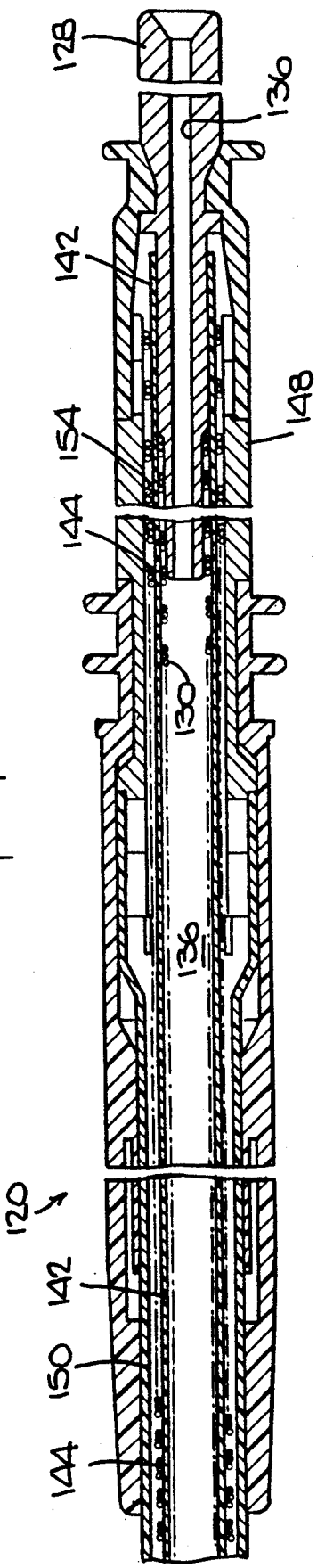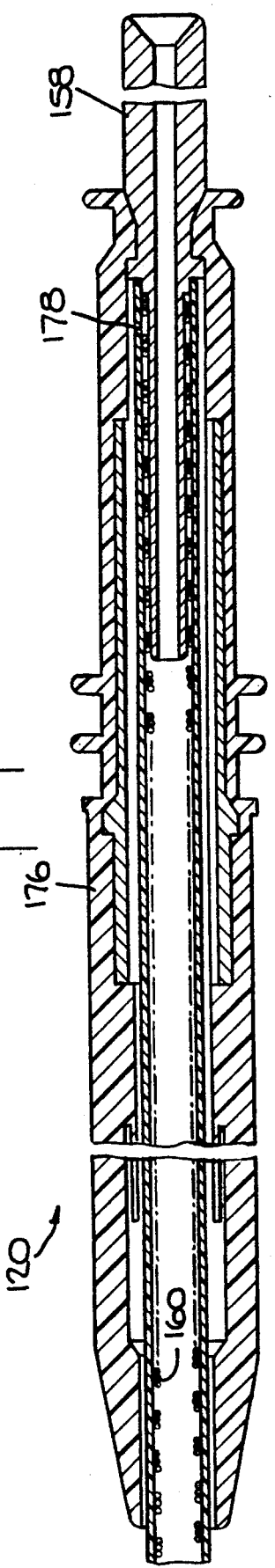

PRESSURE SENSING PACING LEAD

FIELD OF THE INVENTION

This invention is generally directed to an endocardial lead system for use with an implantable heart monitoring and stimulating device for monitoring and treating a malfunctioning heart. More specifically, this invention is directed to an endocardial pacing lead system which includes an integral haemodynamic pressure-sensing electrode therein capable of monitoring blood pressure information within the heart and delivering such information to a haemodynamically responsive cardioverting/defibrillating pacemaker.

BACKGROUND OF THE INVENTION

A detailed history of electrical cardiac stimulators, from the earliest pacemakers capable of delivering electrical stimuli at a fixed rate regardless of the heart's functioning to the modern microprocessor-controlled cardioverting/defibrillating pacemakers capable of delivering measured electrical stimuli based on the haemodynamic state of a patient, is provided in U.S. patent application No. 07/481,364 to K. A. Collins, filed Feb. 16, 1990, and entitled "An Implantable Automatic and Haemodynamically Responsive Cardioverting/Defibrillating Pacemaker." The contents of U.S. patent application No. 07/481,364 are hereby incorporated herein by reference.

The pacemaker of U.S. patent application No. 07/481,364 includes means to overcome many of the problems relating both to the failure to provide necessary electrical therapy, and to the delivery of unnecessary electrical therapy, that arose in earlier systems which relied upon the sensing of blood pressure in the heart as a means for determining the state of cardiac function. It thus also has applicability to the present invention, as will become more apparent below. Similarly, the subjects matter of U.S. patent application No. 07/600,419 to K. A. Collins et al., filed Oct. 19, 1990, and entitled "Implantable Haemodynamically Responsive Cardioverting/Defibrillating Pacemaker," and U.S. patent application No. 07/557,248 to K. A. Collins et al., filed Jul. 24, 1990, and entitled "An Implantable Automatic and Hemodynamically Responsive Cardioverting/Defibrillating Pacemaker With Means For Minimizing Bradycardia Support," also are applicable to the present invention and are therefore also incorporated herein by this reference. The three aforementioned United States patent applications are all assigned to the assignee of the present invention. A brief summary of each of these applications is provided below.

U.S. patent application No. 07/481,364 discloses a cardioverting/defibrillating pacemaker with the ability to sense and respond to haemodynamic compromise. The degree of haemodynamic compromise is determined with the aid of an appropriate algorithm by comparing the derived ventricular filtered peak-to-peak amplitude or derived ventricular peak pressure with programmed values for these parameters.

U.S. patent application No. 07/600,419 discloses, among other innovative concepts, a novel method and means for monitoring both an electrocardiogram (ECG) signal system and a haemodynamic signal system whereby the functioning of the pacemaker device is altered if there is a failure in either of the monitored systems. The disclosed invention ensures that the sensing circuitry for performing the monitoring tasks is operating within defined limits and deactivates either one of the systems that is not within the defined limits. The disclosed invention also ensures that the gain of the sensing amplifiers is maintained within proper limits; and, it uses the unaffected sensing system alone to determine how the device should function in the event one of the systems is not operating within the prescribed limits.

U.S. patent application No. 07/557,248 is directed to a method and apparatus for minimizing the energy required for bradycardia support pacing in order to lengthen battery life. This energy minimization is achieved by sensing the right ventricular pressure (RVP) to determine if a response to bradycardia support pacing is evoked. The bradycardia pacing voltage is reduced to the lowest level it can have while still being able to "capture" the heart. The RVP waveform is monitored and the number of pressure pulses evoked in response to a number of pacing pulses is counted. If at least X pressure pulses are sensed in response to Y pacing pulses, capture is assumed, where X is less than or equal to Y. There are several other embodiments disclosed and claimed which also depend upon the monitoring of right ventrical pressure.

The foregoing Collins and Collins et al. applications all require that haemodynamic inputs be provided to the pacemakers employed therein. Endocardial pacing lead systems equipped with haemodynamic pressure sensors are generally used for this purpose. U.S. Pat. Nos. 4,566,456 to G. Koning et al., 4,708,143 to E. A. Schroeppel, and 4,967,755 to P. J. Pohndorf are representative of patents that disclose endocardial pacing lead systems which are provided with haemodynamic pressure sensors. A brief discussion of each of these patents follows.

The Koning et al. U.S. Pat. No. 4,566,456 discloses a pacer system including a pacemaker and an endocardial sensing/pacing lead. The sensing/pacing lead includes a pressure sensor therein which comprises a piezo-resistive micro-electronic transducer on a chip which is embedded within an elastomeric material. The transducer is secured within an opening in a tubular sheath of the lead. It is mounted on a glass carrier, and four insulated sensor wire conductors are coupled to the glass carrier for connection to a bridge comprised of variable piezo-resistors of the transducer. The four wires extend within the interior of the lead to the proximal end thereof, and a multi-terminal connector is employed at the proximal end of the lead to connect the four wires of the pressure sensor and the electrical sensing/pacing wires of the lead to the pacemaker.

The Schroeppel U.S. Pat. No. 4,708,143 discloses a pacer system including a pacemaker and an endocardial sensing/pacing lead. The sensing/pacing lead includes a pressure sensor incorporated in the form of a piezoelectric bimorph located in the elastomeric body of the lead, between the outer and inner walls thereof. The bimorph includes a pair of piezoelectric ceramic sheets separated by a brass shim. A pair of insulated wires, located in the body of the lead, connect the upper and lower surfaces of the bimorph to corresponding terminals at the proximal end of the lead, for connection to the pacemaker. Alternative pressure sensors in the form of piezoelectric strips constructed of thin film polymers, mounted in the body of the distal portion of the lead in various configurations, are also disclosed.

The Pohndorf U.S. Pat. No. 4,967,755 also discloses an endocardial sensing/pacing lead which includes a haemo-dynamic pressure sensor therein, as well as tip and ring pacing/sensing electrodes. The pressure sensor includes a metallic case, in the shape of one-half of a cylinder, that is positioned within and mechanically and electrically coupled to the ring electrode. A resilient, insulating, elastomeric material, also in the shape of one-half of a cylinder and having a metallic, axially extending tube centered therein and passing therethrough, provides access for a stylet to pass between the sensor body and the ring electrode for fixing the tip electrode in place. The two half-cylinders are positioned within the ring electrode, with their outer planar diameter surfaces in abutment with one another so that, together, they form a full cylinder. The ring electrode is provided with apertures which allow the pressure of surrounding blood to be transmitted to and through the elastomeric material to the outer surface of a diaphram that is welded around an opening in the outer planar surface of the metallic sensor case. A piezoelectric crystal fixed to the inner surface of the diaphram and coupled to electronic circuitry within the metallic sensor case provides an output signal representative of the haemo-dynamic pressure. This output signal is provided across (a) one output lead of the sensor, which lead is connected via one insulated wire of a multi-filar coil wire to one surface of a multiple proximal connector, and (b) the metallic case of the sensor, which case is connected via the ring electrode and the remaining wires of that coil wire to another surface of the proximal connector.

Although the foregoing pressure sensor equipped endocardial pacing lead systems are capable of performing their intended functions, the pressure sensing portions thereof are less than optimal with respect to sensor sensitivity, sensor output, durability of the pressure sensor, and efficient use of connective wiring to prevent interference with stylet insertion during implantation.

It is, therefore, a primary object of the present invention to provide an endocardial lead having an improved non-integral haemodynamic pressure sensor therein.

It is another object of the present invention to provide an improved endocardial lead that incorporates therein sensing/pacing and defibrillating electrodes in combination with an improved haemodynamic pressure sensor.

It is a further object of the present invention to provide an improved endocardial lead that incorporates therein bipolar sensing/pacing electrodes in combination with a haemodynamic pressure sensor.

Further objects and advantages of the present invention will become apparent as the following description proceeds.

SUMMARY OF THE INVENTION

Briefly stated, and in accordance with one embodiment of the present invention, an elongate endocardial lead is provided which includes at least one distal electrode for sensing electrical activity in, and delivering electrical pacing pulses to, a patient's malfunctioning heart, a plurality of proximal terminal pins for coupling the lead to a pacemaker device, and a distal pressure sensor for sensing haemodynamic pressure within the heart. The pressure sensor comprises an integrated circuit chip having a piezo-resistive diaphragm and a non-conductive base member, with the diaphragm being carried by the base member and having a pressure sensing area on an outer surface thereof exposed to ambient pressure. The base member and diaphragm are constructed and arranged so as to form a hermetically sealed chamber therebetween, with the chamber being at substantially atmospheric pressure and being substantially coextensive with the pressure sensing area. The lead further includes means for coupling the integrated circuit chip across first and second ones of the proximal terminal pins. Preferably the distal electrode includes means therein for fixing the electrode to tissue in the patient's heart, and the integrated circuit chip includes first and second contact means for connecting the chip to an electrical circuit. In this case the coupling means includes inner and outer coaxial coil wires separated by a layer of insulating material, with the inner and outer coil wires respectively connecting the first terminal pin to the first contact means and the second terminal pin to the second contact means, so that the inner coil wire forms a coaxial central lumen in the lead throughout a major portion of the length thereof to facilitate passage of a stylet therethrough for actuating the fixing means. It is also preferred that the base member and the diaphragm include planar surfaces in abutment with one another, that the planar surface of the base member be recessed in the area of the hermetically sealed chamber, and that the planar surfaces of the base member and the diaphragm be anodically bonded to one another peripherally of the recess in the planar surface of the base member to form the hermetically sealed chamber.

In accordance with another embodiment of the present invention, an elongate endocardial lead is provided having at least one distal electrode for sensing electrical activity in, and delivering pacing pulses to, a patient's malfunctioning heart, a plurality of proximal terminal pins for coupling the lead to a pacemaker device, a distal pressure sensor for sensing haemodynamic pressure within the heart, and means for coupling the pressure sensor across first and second ones of the proximal terminal pins. The distal electrode includes means therein for fixing the electrode to heart tissue. The pressure sensor includes a piezo-resistive diaphragm, a non-conductive base member supporting the diaphragm for limited flexing movement relative to the base member in response to pressure variations on the diaphragm, and first and second contact means for connecting the pressure sensor to an electrical circuit. The coupling means includes inner and outer coaxial coil wires separated by a layer of insulating material, with the inner and outer coil wires respectively connecting the first terminal pin to the first contact means and the second terminal pin to the second contact means, so that the inner coil wire forms a coaxial central lumen in the lead throughout a major portion of the length thereof to facilitate passage of a stylet therethrough for actuating the fixing means. Preferably, the diaphragm of the pressure sensor includes a pressure sensing area on an outer surface thereof, the base member and the diaphragm include planar surfaces in abutment with one another, and the planar surface of the base member is recessed substantially coextensively with the pressure sensing area of the diaphragm to facilitate the flexing movement of the diaphragm. It is also preferred that the lead include a distal ring electrode for sensing electrical activity in, and delivering pacing pulses to the patient's heart. The ring electrode may comprise an enlarged, metallic, braided electrode for delivering cardioversion shock therapy to the patient's heart in addition to or as an alternative to delivering pacing therapy to the heart. Where a distal ring electrode is employed, the lead desirably includes a third proximal pin, and either a third coaxial coil wire, or a coaxial braided wire in the case of a braided ring electrode, is employed to interconnect the third proximal pin and the distal ring electrode.

The utilization and advantages of a braid electrode are described in U.S. Pat. No. 5,005,587 to Steven Scott, dated Apr. 9, 1991, and entitled "Braid Electrode Leads And Catheters And Methods For Using The Same". Briefly, U.S. Pat. No. 5,005,587 is directed to a lead for implantation in the body for applying a therapeutic shock from a source of electrical energy. The lead includes an electrically conductive braid which increases the surface area of conduction for application of the shock which, in turn, enhances the efficiency of the applied shock. Although an increased surface area electrode is beneficial to the application of any utilized therapy, it is especially useful in achieving the high power requirement of a defibrillating shock. U.S. Pat. No. 5,005,587 is owned by the assignee of the present invention and is incorporated herein by reference.

The present invention has applications which can be implemented in a ventricular catheter, or an atrial catheter, or a dual chamber catheter. Furthermore, the disclosed lead system can be used in conjunction with either an epicardial patch electrode, a subcutaneous patch electrode, or other implanted electrodes, such as the conductive case of a pacemaker/defibrillator.

BRIEF DESCRIPTION OF THE DRAWINGS

While the specification concludes with claims particularly pointing out and distinctly claiming the subject matter regarded as the invention herein, it is believed that the present invention will be more readily understood upon consideration of the following description, taken in conjunction with the accompanying drawings, wherein:

FIG. 1 is a plan view of a unipolar endocardial pacing lead having a haemodynamic pressure sensor therein in accordance with one embodiment of the present invention;

FIG. 2 is an enlarged cross-sectional view of the proximal end of the lead, taken along the line 2—2 of FIG. 1;

FIG. 3 is an enlarged cross-sectional view of the distal end of the lead, taken along the line 3—3 of FIG. 1;

FIG. 4 is an enlarged plan view of a portion of the lead shown in FIG. 1, showing details of the pressure sensor thereof;

FIG. 5 is an enlarged, exploded perspective view of the pressure sensor portion of the lead of FIG. 1, showing details of the mounting of a pressure sensor chip therein;

FIG. 6 is a top plan view of the pressure sensor shown in FIG. 5;

FIG. 7 is a sectional elevation view of the pressure sensor, taken along the line 7—7 of FIG. 6;

FIG. 8 is a sectional elevation view of the pressure sensor, taken along the line 8—8 of FIG. 7;

FIG. 11 is a plan view, with parts cut away for clarity, of a bipolar endocardial lead having a haemodynamic pressure sensor therein, in accordance with an alternate embodiment of the present invention;

FIG. 12 is a cross-sectional view, taken along the line 12—12 of FIG. 11, of a first proximal portion of the lead shown in FIG. 11;

FIG. 13 is a cross-sectional view, taken along the line 13—13 of FIG. 11, of a second proximal portion of the lead shown in FIG. 11;

FIG. 15 is a cross-sectional view, taken along the line 15—15 of FIG. 11, of the distal tip electrode portion of the lead shown in FIG. 11;

FIG. 16 is a cross-sectional view, similar to FIG. 15, but showing a tip electrode anchoring screw of the lead in an extended condition;

FIGS. 18-20 are sectional elevation views, taken along the lines 18—18, 19—19 and 20—20, respectively, of the lead shown in FIG. 17.

DETAILED DESCRIPTION OF THE DRAWINGS

Figure 10:
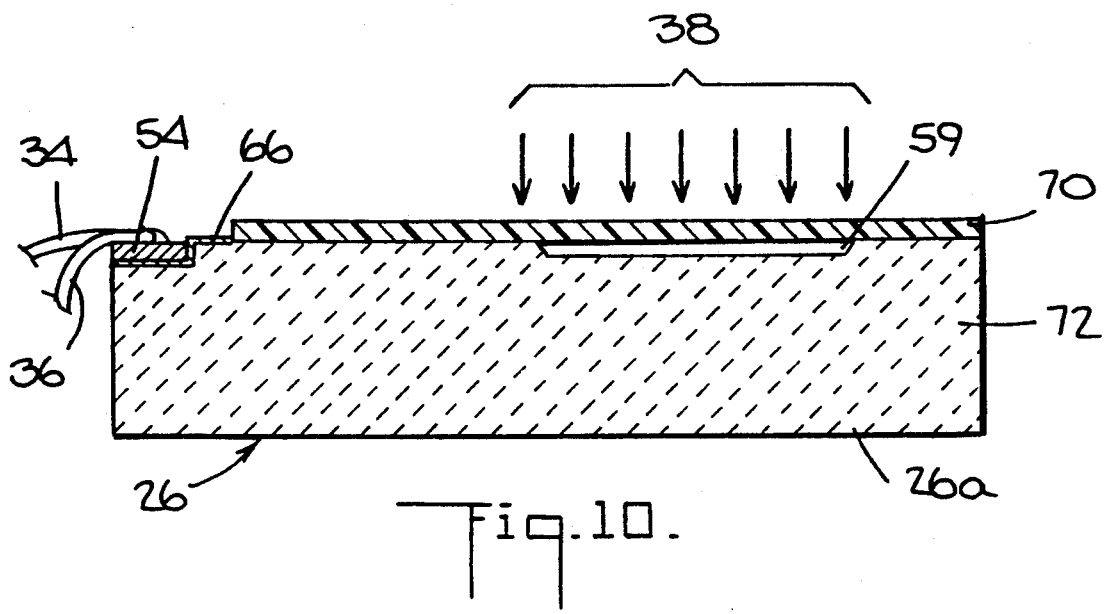
FIG. 10 is a sectional elevation view of the pressure sensor chip, taken along the line 10—10 of FIG. 9.

Referring specifically to FIG. 1, a unipolar haemodynamic pressure sensing endocardial lead, generally designated 20, is illustrated. Lead 20 has a distal end 21 and a proximal end 23. Formed on distal end 21 is a pacing and sensing tip electrode 22, as is well known in the art. Proximal end 23 includes a first terminal pin 24 which is used to couple lead 20 to an electrical device such as a pacemaker (not shown) for sensing electrical signals from and delivering pacing pulses to a malfunctioning heart (not shown). A second terminal pin 25, which is coaxial with terminal pin 24, is also provided for purposes to be discussed in greater detail hereinafter.

Lead 20 also comprises an insulator housing 28 which supports a pressure sensor, shown generally at 26. Pressure sensor 26 is fixedly supported in a recessed portion of housing 28 to permit the pressure sensor to be mounted as an integral portion of lead 20, as will also be discussed in greater detail hereinafter.

Referring to FIGS. 2 and 3, together, terminal pin 24 is connected to tip electrode 22 by means of an inner quadrifilar coil conductor comprising a coil wire 30 (FIG. 2) that is welded to terminal pin 24 at one of its ends and is also welded at the other of its ends (FIG. 3) to one end of a metallic inner tube 46. A coil wire 31 welded to the other end of tube 46 extends from tube 46 to the tip electrode 22 and is crimped thereto to form an electrical connection to the tip electrode. Similarly, and referring to FIGS. 2-4, together, terminal pin 25 is connected to one electrical bond wire or contact wire 34 (FIG. 4) of pressure sensor 26 by means of a coil wire 32 one end 32b of which (FIG. 2) is welded to the inner surface of terminal pin 25 and the other end 32a (FIG. 3) of which is welded to a metallic band 42, to which contact wire 34 is welded. A second bond wire or contact wire 36 (FIG. 4) of pressure sensor 26 is welded to metal inner tube 36 to interconnect pressure sensor 26 across terminal pins 24 and 25.

The location of pressure sensor 26 within insulator housing 28 is illustrated in FIGS. 4-8. Pressure sensor 26 is affixed within a recessed region or portion 41 of insulating housing 28, typically by potting it in position with epoxy resin 71 (FIG. 4). Pressure sensor 26 preferably includes an integrated circuit chip 26a which contains a pressure sensing area 38 (FIG. 6) therein that is left exposed when the pressure sensor is potted in place.

As best seen in FIG. 5, which comprises an exploded view of the integrated circuit chip 26a portion of pressure sensor 26 relative to insulator housing 28 and other nearby components, insulator housing 28 is provided with a reduced diameter portion 28a therein, which together with a shoulder 28b of the housing forms a seat for the metallic band 42. An etched aperature or opening 44 is provided through the annular wall of housing 28 to provide communication between region 41 thereof and a flattened portion 46a (see FIGS. 6-8) on the outer surface of inner tube 46. Additionally, a flattened portion 48 is formed on the outer surface of metallic band 42 Aperture 44 and flattened portions 46a and 48 are implemented to simplify electrical coupling between the chip 26a of pressure sensor 26 and inner tube 46 and metallic band 42, via contact wires 36 and 34, respectively, as indicated earlier.

FIG. 6 represents a top plan view of the components shown in FIG. 5, showing the placement of the integrated circuit chip 26a in the region 41 of the housing 28. It should be noted that region 41 is an etched portion of housing 28 which has a depth intermediate the radially inner end of etched aperture 44 and the unetched radially outer circumference 43 of housing 28.

The depths of flattened portions 46a and 48, region 41 and aperture 44 are apparent from an inspection of FIG. 7. As best seen in FIGS. 6 and 7, when the integrated circuit chip 26a is positioned in region 41 of housing 28, contact wire 34 is welded to area 48 of metallic band 42 to provide an electrical connection between the metallic band 42 and the chip, and contact wire 36 is welded to area 46a of inner tube 46 to provide an electrical connection, through aperture 44, between the inner tube 46 and the chip.

It will be apparent to those skilled in the art that the diameters of the components can vary but should be made as small as possible to simplify insertion of the lead 20 into the patient's heart.

Figure 9:
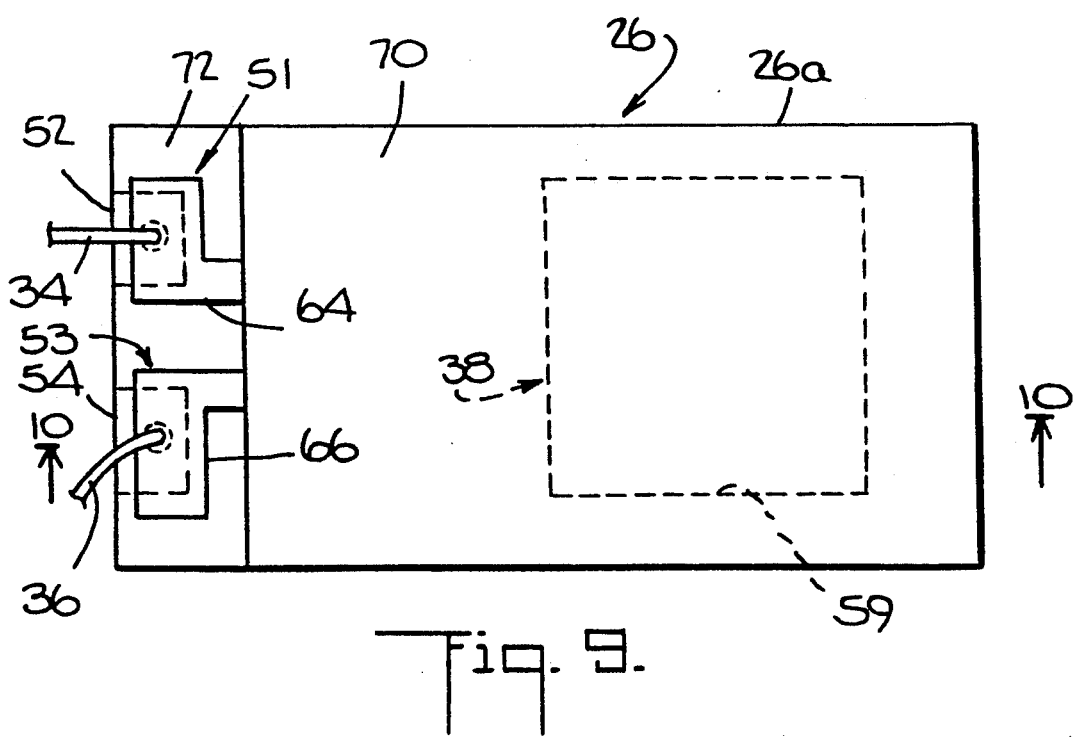
FIG. 9 is an enlarged top plan view of the pressure sensor chip shown in FIG. 5.
Figure 14:
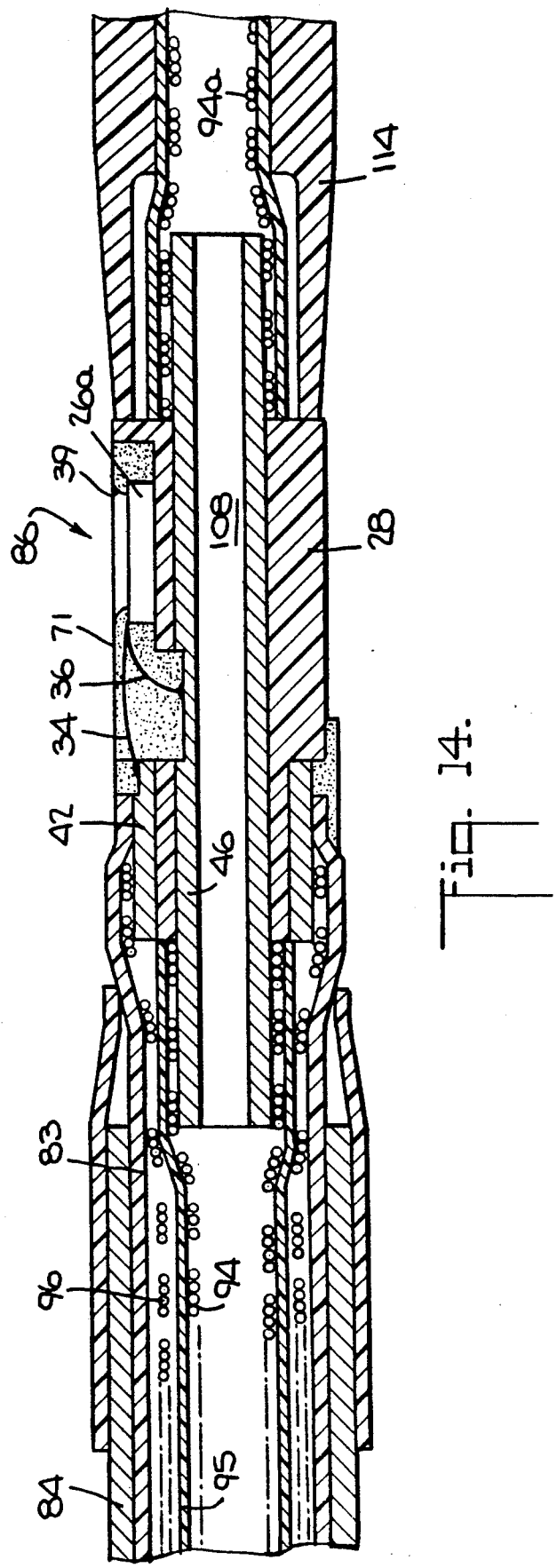
FIG. 14 is a cross-sectional view, taken along the line 14—14 of FIG. 11, of the pressure sensor in the distal portion of the lead shown in FIG. 11.
Figure 17:
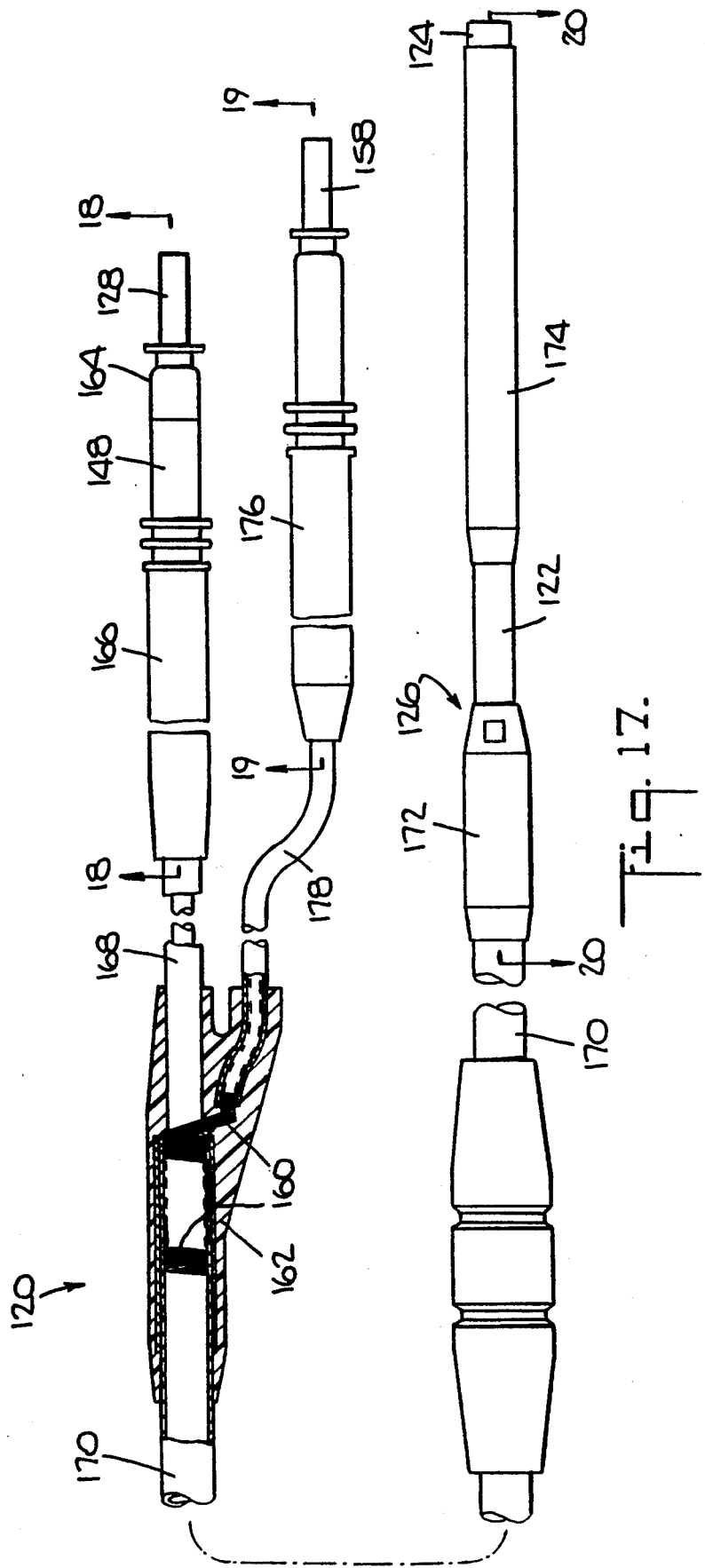
FIG. 17 is a plan view, with parts cut away for clarity, of another bipolar endocardial lead, having a haemodynamic pressure sensor in accordance with a third embodiment of the invention.
Figure 20:
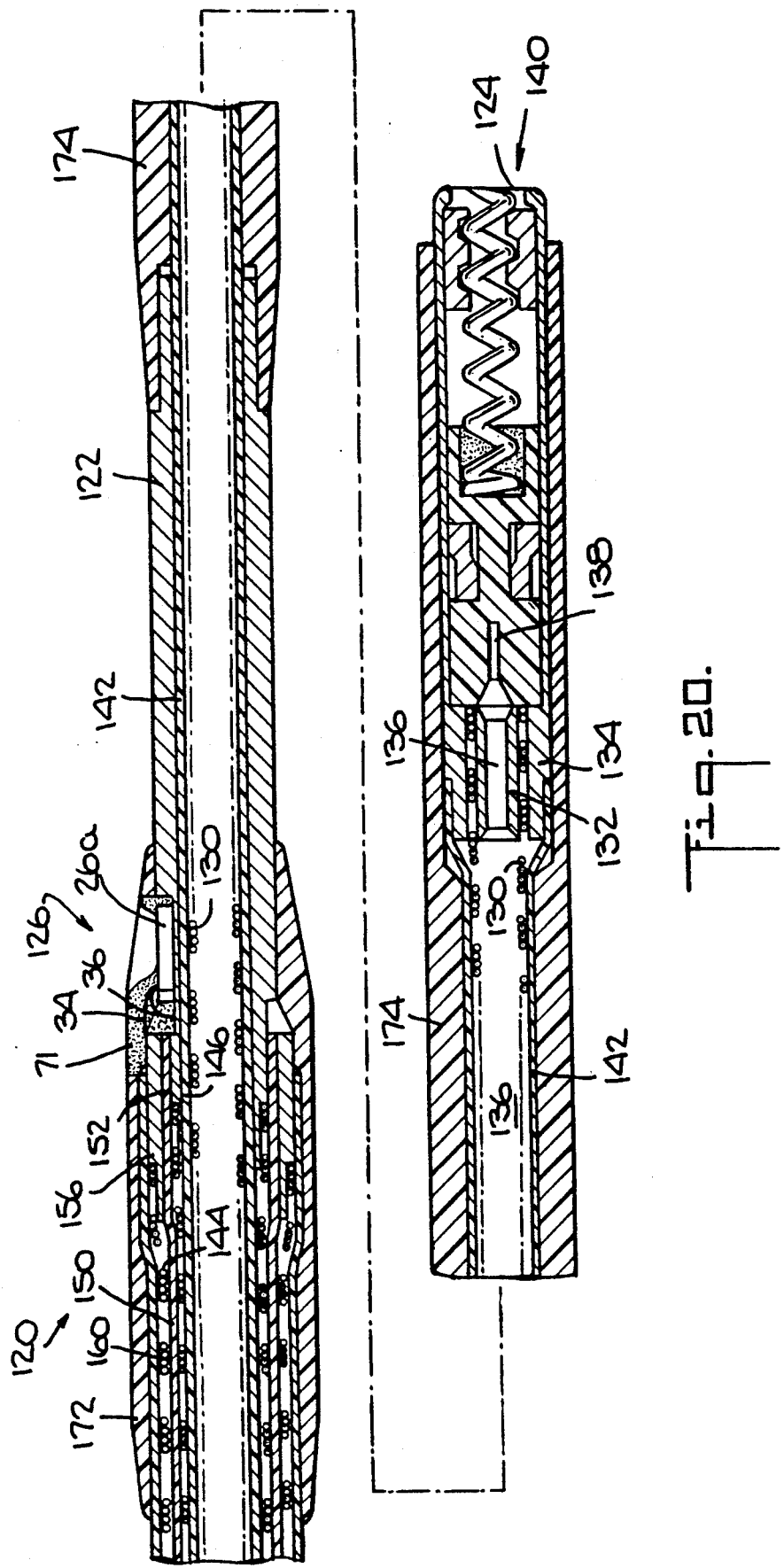

Referring specifically to FIGS. 9 and 10, the integrated circuit chip 26a, comprises a thin-film layer 70 which overlays and is anodically bonded to the outer portion of an etched, hollowed-out, upper surface of a restraint or base member 72 so as to form a hermetically sealed chamber 59 therebetween having a pressure of 1 atmosphere therein. The area of layer 70 that is coextensive with chamber 59 comprises a pressure sensing diaphragm area 38. Layer 70 preferably comprises a piezoresistive material that changes resistance with pressure, for example monocrystalline silicon that is doped in the regions of greatest stress (i.e., adjacent the margins of chamber 59). Similarly, restraint 72 can consist of various non-conductive materials such as silicon, PYREX glass, or the like.

A first contact 51 of pressure-sensing integrated circuit chip 26a is formed by a metallic connecting strip 64 extending outwardly from under layer 70 and overlapping (or underlying) at least a portion of a metallic contact pad 52. Similarly, a second contact 53 is formed by a metallic connecting strip 66 extending outwardly from under layer 70 and overlaying (or underlying) at least a portion of a metallic contact pad 54. Metallic contact pad 52 and metallic contact pad 54 are preferably comprised of chrome, but other appropriate metals may be used. Metallic connecting strips 64 and 66 are preferably comprised of gold, but again various other appropriate metals may be used.

Although specific dimensions are not critical for purposes of the present invention, the integrated circuit pressure-sensing chip 26a must have small enough dimensions to fit within the body of lead 20. The chip utilized by the inventor during the development of the present invention had a length of 1.6 millimeters, a width of 1 millimeter and a thickness of 295 microns (0.295 mm). The 295 micron thickness consisted overwhelmingly of the restraint 72, covered with a very thin piezo-resistive layer 70 having a thickness varying between one and two microns.

As illustrated in FIG. 4, pressure sensing chip 26a is potted to insulator housing 28 by epoxy resin 71, which covers contact wires 34 and 36, etched aperture 44, flattened portion 48 of metallic band 42, and all portions of pressure sensor 26, with the exception of a window region 39. Window region 39 allows pressure sensing diaphragm area 38 to remain exposed.

As shown in FIG. 10, hermetically sealed chamber 59 is located directly below pressure-sensing diaphragm area 38, and chamber 59 is located directly beneath that portion of chip 26a which is left exposed by epoxy window region 39 (FIG. 1) during the epoxy resin bonding (potting) of chip 26a to insulator housing 28. Preferably, chamber 59 is sufficiently deep (e.g. 15-30 microns) so that the diaphragm area 38 does not come in contact with the upper surface of base member 72 within the chamber 59 under the conditions of pressure encountered during normal operation of pressure sensor 26.

The unipolar electrode pressure sensor embodiment of the lead 20 according to the present invention, disclosed in FIGS. 1-10, is useful both for therapeutic and for diagnostic purposes. This first embodiment may be used in conjunction with either an external monitor/pacer (with the lead percutaneously implanted) or with an implanted monitoring/pacing device. It may also be used to provide information on sensor chronic performance with respect to endothelial encapsulation, scarring, etc. As previously mentioned, atrial blood pressure or ventricular blood pressure can be measured depending on the chamber in which the pressure sensor is positioned.

Referring now specifically to FIGS. 11-16, a second embodiment of the present invention is disclosed. This embodiment comprises a bipolar haemodynamic pressure sensing endocardial lead, shown generally at 80. Lead 80 includes a tip electrode 82 and a metallic braid electrode 84 for sensing electrical activity in the heart and applying either pacing pulses or cardioversion shocks to the heart, as necessary. Lead 80 also includes a pressure sensor, shown generally at 86, for sensing blood pressure in the heart.

Braid electrode 84 is electrically connected to terminal pin 88 by means of a metallic braided conductor having a portion 84a which extends from electrode 84, under an insulating sheath 95 and about an insulating tube 83 of lead 80, to an insulated bifurcation 87, at which a braid portion 84b separates from insulating tube 83 and extends to, and is welded to, terminal pin 88. Terminal pin 88, in turn, is selectively connectable to pacemaker and cardioversion circuitry (not shown). Braid electrode 84 can be used for sensing purposes, and as one electrode of a bipolar pair for applying pacing pulses, cardioverting therapy and defibrillating shocks to the heart. Alternatively, an exposed, elongate, coil wire conductor (not shown) can be employed in place of the metallic braid electrode 84 for similar purposes. Insulating members 87a, 87b and 87c cover the metallic braid portion 84b enroute from bifrcation 87 to terminal pin 88.

Pressure sensor 86 preferably includes an integrated circuit chip 26a of the type illustrated in FIGS. 9 and 10. Chip 26a is preferably mounted in insulator housing 28 and coupled to lead 80 in a manner similar to that described above in connection with the first embodiment (FIGS. 1-10) of the present invention. Thus, lead 80 is provided at its proximal end with two additional terminal pins 90 and 92 that are electrically connected to inner and outer quadrifilar coil wires 94 and 96, respectively (FIG. 12), which are separated by an insulating layer 95. The inner coil wire 94, in turn, is electrically connected to one end of metallic inner tube 46, the other end of which is electrically coupled to tip electrode 82 by a length of coil wire 94a. An insulating sheath 91 surrounds the proximal end portion of coil wire 94 at its connection area to terminal pin 90, and axially separates the terminal pins 91 and 92. Similarly an insulation sheath 93 surrounds the connection area of the proximal end portion of coil wire 96 and terminal pin 92. As in the case of the FIGS. 1-10 embodiment, contact wire 36 of chip 26a electrically connects the chip to inner tube 46. Similarly, contact wire 34 of chip 26a electrically connects the chip to metallic band 42 which, in turn, has one end of the outer coil wire 96 welded to it. The other end of the coil wire 96 is connected to terminal pin 92, as indicated above. Thus chip 26a is connected between terminal pins 90 and 92 via coil wires 94 and 96, respectively, inner tube 46, metallic band 42, and contact wires 36 and 34. Tip electrode 82 is also connected to terminal pin 90, and braid electrode 84 is connected to terminal pin 88. The result is a bipolar electrode lead in which electrical pacing and sensing occurs between terminal pins 88 and 90, and in which pressure is sensed between terminal pins 90 and 92, with terminal pin 90 and coil wire 94 being connected to and serving both the chip 26a and the tip electrode 82.

Referring now to FIGS. 15 and 16, the endocardial lead 80 is provided with an active fixation device, shown generally at 100. The fixation device 100 includes a helical spring 102 that is movable between an inactive or retracted position, at which it is within the tip electrode 82, as shown in FIG. 15, and an active or extended position, shown in FIG. 16, at which it extends from tip electrode 82 into cardiac tissue 104. A stylet 106, which may be introduced through a lumen 108 that extends within lead 80 from terminal pin 90 (FIG. 12) to the distal area adjacent tip electrode 82 (FIG. 16), is employed to move helical spring 102 between its inactive and active positions. Stylet 106 engages a slot 110 to rotate a driving member 112 and move the helical coil 102 between its extended and retracted positions during implantation and removal of the lead 80, in a manner well known in the art.

Referring now to FIGS. 17-20, a third embodiment of the present invention is disclosed. This embodiment comprises a bipolar haemodynamic pressure sensing endocardial lead, shown generally at 120. Lead 120 differs from lead 80 of FIGS. 11-16, among other things, in that a conventional pacing/sensing ring electrode 122 is employed therein in place of the braid electrode 84 of lead 80. It also differs in the manner of mounting integrated circuit chip 26a on the endocardial lead, and in the manner of connecting chip 26a to its proximal terminal pins.

As mentioned above, lead 120 includes ring electrode 122 as well as tip electrode 124 at its distal end for sensing electrical activity in the heart and applying pacing pulses to the heart, as necessary. Lead 120 also includes a pressure sensor, shown generally at 126 and including integrated circuit chip 26a, for sensing blood pressure in the heart.

Tip electrode 124 is electrically connected to a terminal pin 128 at the proximal end of the lead 120 by means of an inner coil wire 130. Coil wire 130 is crimped at its distal end between an annular ferrule 132 and an extension 134 of tip electrode 124 so as to make firm electrical contact with the electrode. The proximal end of inner coil wire 130 is welded to the terminal pin 128. Lead 120 is provided with a lumen 136 which extends within the terminal pin 128 and throughout the length of inner coil wire 130 in order to provide access for a stylet (not shown) to actuate a fixation device, shown generally at 140, via a slot 138. The operation of the fixation device 140 is similar to that described earlier herein in connection with the embodiment shown in FIGS. 11 through 16.

The inner coil wire 130 is surrounded by an insulating tube or layer 142 through essentially the entire length of lead 120 to prevent contact between the inner coil wire and an intermediate coil wire 144, the distal end of which is welded to an extension 146 on ring electrode 122 to electrically connect the ring electrode with a terminal pin 148 at the proximal end of lead 120. Coil wire 144 also connects the contact wire 36 of chip 26a to terminal pin 148 due to the fact that the contact wire 36 is conductably fastened to the extension 146 of ring terminal 122.

The intermediate coil wire 144 is surrounded by a second insulating layer or tube 150, the distal end 152 of which also surrounds the extension 146 of ring terminal 122. The proximal end portion 154 of intermediate coil wire 144 is welded or otherwise electrically conductively fastened to the interior of terminal pin 148 to provide good electrical conductivity, via intermediate coil wire 144, between the pin 148 and both the ring terminal 122 and the contact wire 36 of integrated circuit chip 26a.

The chip 26a is preferably potted in place on the extension 146 of ring electrode 122 by epoxy resin 71. A metallic ring 156, mounted on the distal portion 152 of insulating layer 150, is provided. Contact wire 34 of integrated circuit chip 26a is conductively fastened to metallic ring 156, and ring 156, in turn, is electrically connected to a third terminal pin 158 via an outer coil wire 160. The outer coil wire 160 extends coaxially with the intermediate and inner coil wires 144 and 130, respectively, throughout most of the length of lead 120 until it reaches an insulated bifurcation 162, at which it separates from the path of the inner and intermediate coil wires and proceeds on a separate path to the terminal pin 158. The various terminal pins 128, 148 and 158 are selectively connectable to pacemaker circuitry (not shown).

Insulating sheaths 164, 166, 168, 170, 172, 174, 176 and 178 surround the various internal parts of the lead 120 to prevent electrical contact between body parts and the interior of lead 120, other than where intended, and to prevent ingress of body fluids into the interior of the lead.

It will be apparent from the foregoing description that the present invention provides an endocardial lead having an improved, integral haemodynamic pressure sensor therein. The arrangement of the integrated circuit chip of the pressure sensor provides for high sensitivity and linearity, and the efficient use of the wiring within the lead to connect the pressure sensor to its terminal pins minimizes obstructions within the lead, facilitating the introduction of a stylet therein in connection with installation of the lead into and removal of the lead from a patient. Moreover, the lead can incorporate either unipolar or bipolar sensing/pacing electrodes in combination with the improved pressure sensor, and can include a defibrillation electrode therein.

While there have been shown and described what are presently considered to be the preferred embodiments of this invention, it will be obvious to those skilled in the art that various changes and modifications may be made without departing from the broader aspects of this invention. It is, therefore, aimed in the appended claims to cover all such changes and modifications as fall within the true spirit and scope of this invention.

What is claimed is:

1. An elongate endocardial lead including at least one distal electrode for sensing electrical activity in, and delivering electrical pacing pulses to, a patient's malfunctioning heart, a plurality of proximal terminal pins for coupling said lead to a pacemaker device, and a distal pressure sensor for sensing haemodynamic pressure within the heart,
    said pressure sensor comprising an integrated circuit chip having a layer of piezo-resistive material and a non-conductive base member, said layer being carried by said base member and having a pressure sensing diaphragm area therein exposed to ambient pressure, said base member and said layer being constructed and arranged so as to form a hermetically sealed chamber therebetween, said chamber being at substantially atmospheric pressure and being substantially coextensive with said pressure sensing diaphragm area;
    said lead further including means for coupling said integrated circuit chip across first and second ones of said proximal terminal pins.

2. An endocardial lead according to claim 1, wherein said distal electrode includes means therein for fixing said electrode to tissue in the patient's heart, wherein said integrated circuit chip includes first and second contact means for connecting said chip to an electrical circuit, and wherein said coupling means includes inner and outer coaxial coil wires separated by a layer of insulating material, said inner and outer coil wires respectively connecting said first terminal pin to said first contact means and said second terminal pin to said second contact means, said inner coil wire forming a coaxial central lumen in said lead throughout a major portion of the length thereof to facilitate passage of a stylet therethrough for actuating said fixing means.

3. An endocardial lead according to claim 2, wherein said base member and said layer include planar surfaces in abutment with one another, wherein the planar surface of said base member is recessed in the area of said hermetically sealed chamber, and wherein said planar surfaces of said base member and said layer are anodically bonded to one another peripherally of the recess in said planar surface of said base member to form said hermetically sealed chamber.

4. An endocardial lead according to claim 1, wherein said base member and said layer include planar surfaces in abutment with one another, wherein the planar surface of said base member is recessed in the area of said hermetically sealed chamber, and wherein said planar surfaces of said base member and said layer are anodically bonded to one another peripherally of the recess in said planar surface of said base member to form said hermetically sealed chamber.

5. An elongate, generally cylindrical, endocardial lead having at least one distal electrode for sensing electrical activity in, and delivering pacing pulses to, a patient's malfunctioning heart, a plurality of proximal terminal pins for coupling said lead to a pacemaker device, a distal pressure sensor, proximal of said electrode, for sensing haemodynamic pressure within the heart, and means for coupling said pressure sensor across first and second ones of said proximal terminal pins,
    said distal electrode including rotatable active fixation means therein for fixing said electrode to heart tissue;
    said pressure sensor including a layer of piezo-resistive material, a non-conductive base member supporting said layer of piezo-resistive material for limited flexing movement relative to said base member in response to pressure variations on said layer of piezo-resistive material, and first and second contact means for connecting said pressure sensor to an electrical circuit;
    said coupling means including inner and outer coaxial coil wires separated by a layer of insulating material, said inner and outer coil wires respectively connecting said first terminal pin to said first contact means and said second terminal pin to said second contact means, said lead having a coaxial central lumen therein extending throughout the entire length thereof to facilitate passage of a stylet therethrough and rotation of the stylet therein in order to rotate said active fixation means and fix said electrode to heart tissue;
    wherein said layer of piezo-resistive material of said pressure sensor includes a pressure sensing diaphragm area therein, wherein said base member and said layer of piezo-resistive material include planar surfaces in abutment with one another, and wherein the planar surfaces of said base member is recessed substantially coextensively with said pressure sensing diaphragm area to facilitate said flexing movement.

6. An endocardial lead according to any one of claims 1–4 and 5, wherein said at least one distal electrode comprises a tip electrode, and wherein said lead further includes a distal ring electrode for sensing electrical activity in, and delivering pacing pulses to, the patient's heart.

7. An endocardial lead according to any one of claims 1–4 and 5 wherein said at least one distal electrode comprises a tip electrode, and wherein said lead further includes an enlarged metallic, braided, distal ring electrode for delivering cardioversion shock therapy to the patient's heart.

8. An endocardial lead according to any one of claims 1–4 and 5, wherein said at least one distal electrode comprises a tip electrode, and wherein said tip electrode is coupled to one of said first and second proximal pins.

9. An endocardial lead according to any one of claims 2 and 5, wherein said at least one distal electrode comprises a tip electrode, and wherein said tip electrode is coupled to said first proximal pin by a conductive path which includes said inner coil wire.

10. An endocardial lead according to claim 9, wherein said lead further includes a distal ring electrode for sensing electrical activity in, and delivering pacing pulses to, the patient's heart, and a third proximal pin, and wherein said distal ring electrode is coupled to said third proximal pin by a conductive path which includes a third coil wire that surrounds said outer coil wire for a major portion of the length of said lead and is separated therefrom by a layer of insulating material.

11. An endocardial lead according to claim 9, wherein said lead further includes an enlarged metallic, braided, distal ring electrode for delivering cardioversion shock therapy to the patient's heart, and a third proximal pin, and wherein said distal ring electrode is coupled to said third proximal pin by a conductive path which includes a braided conductor that surrounds said outer coil wire for a major portion of the length of said lead and is separated from said outer coil wire by a layer of insulating material.

* * * * *